(12) United States Patent
Bonnet

(10) Patent No.: US 7,884,943 B2
(45) Date of Patent: Feb. 8, 2011

(54) BI-DIRECTIONAL REFLECTANCE DISTRIBUTION MEASURING INSTRUMENT

(75) Inventor: Gerhard Bonnet, Kaiserslautern (DE)

(73) Assignee: Spheron VR AG, Waldfischbach-Burgalben (DE)

( * ) Notice: Subject to any disclaimer, the term of this patent is extended or adjusted under 35 U.S.C. 154(b) by 98 days.

(21) Appl. No.: 12/094,443

(22) PCT Filed: Nov. 17, 2006

(86) PCT No.: PCT/DE2006/002017

§ 371 (c)(1),
(2), (4) Date: Jul. 7, 2008

(87) PCT Pub. No.: WO2007/059737

PCT Pub. Date: May 31, 2007

(65) Prior Publication Data

US 2008/0304070 A1 Dec. 11, 2008

(30) Foreign Application Priority Data

Nov. 23, 2005 (DE) ........................ 10 2005 056 106

(51) Int. Cl.
*G01N 21/47* (2006.01)
(52) U.S. Cl. ..................................................... 356/446
(58) Field of Classification Search ........................ None
See application file for complete search history.

(56) References Cited

U.S. PATENT DOCUMENTS

| 5,367,873 | A | 11/1994 | Barcza et al. | |
|---|---|---|---|---|
| 5,637,873 | A | 6/1997 | Davis et al. | |
| 5,729,640 | A | 3/1998 | Castonguay | |
| 6,844,931 | B2 * | 1/2005 | Ehbets | 356/328 |
| 2002/0080357 | A1 * | 6/2002 | Dana | 356/445 |
| 2003/0002038 | A1 * | 1/2003 | Mawatari | 356/300 |
| 2006/0239547 | A1 * | 10/2006 | Robinson et al. | 382/162 |

FOREIGN PATENT DOCUMENTS

| DE | 102 20 872 | 11/2003 |
|---|---|---|
| EP | 0 693 179 | 4/1994 |
| WO | 2004/076993 | 9/2004 |

* cited by examiner

*Primary Examiner*—Gregory J Toatley
*Assistant Examiner*—Amanda H Merlino
(74) *Attorney, Agent, or Firm*—Baker & Daniels LLP

(57) ABSTRACT

The invention concerns a bidirectional reflectance distribution meter having a light source which illuminates a sample using pre-determinable elevation and a light receiver, which can be moved relative to the light source in order to receive light from the sample. To this end, it has been designed that the light receiver comprises several receiver elements to collect simultaneously a broad elevation angle range, and that at least one of the light receiver element and the light source is movable around an axis that extends generally vertical to the sample.

19 Claims, 2 Drawing Sheets

BI-DIRECTIONAL REFLECTANCE DISTRIBUTION MEASURING INSTRUMENT

CROSS-REFERENCE TO RELATED APPLICATION

Figure 1:
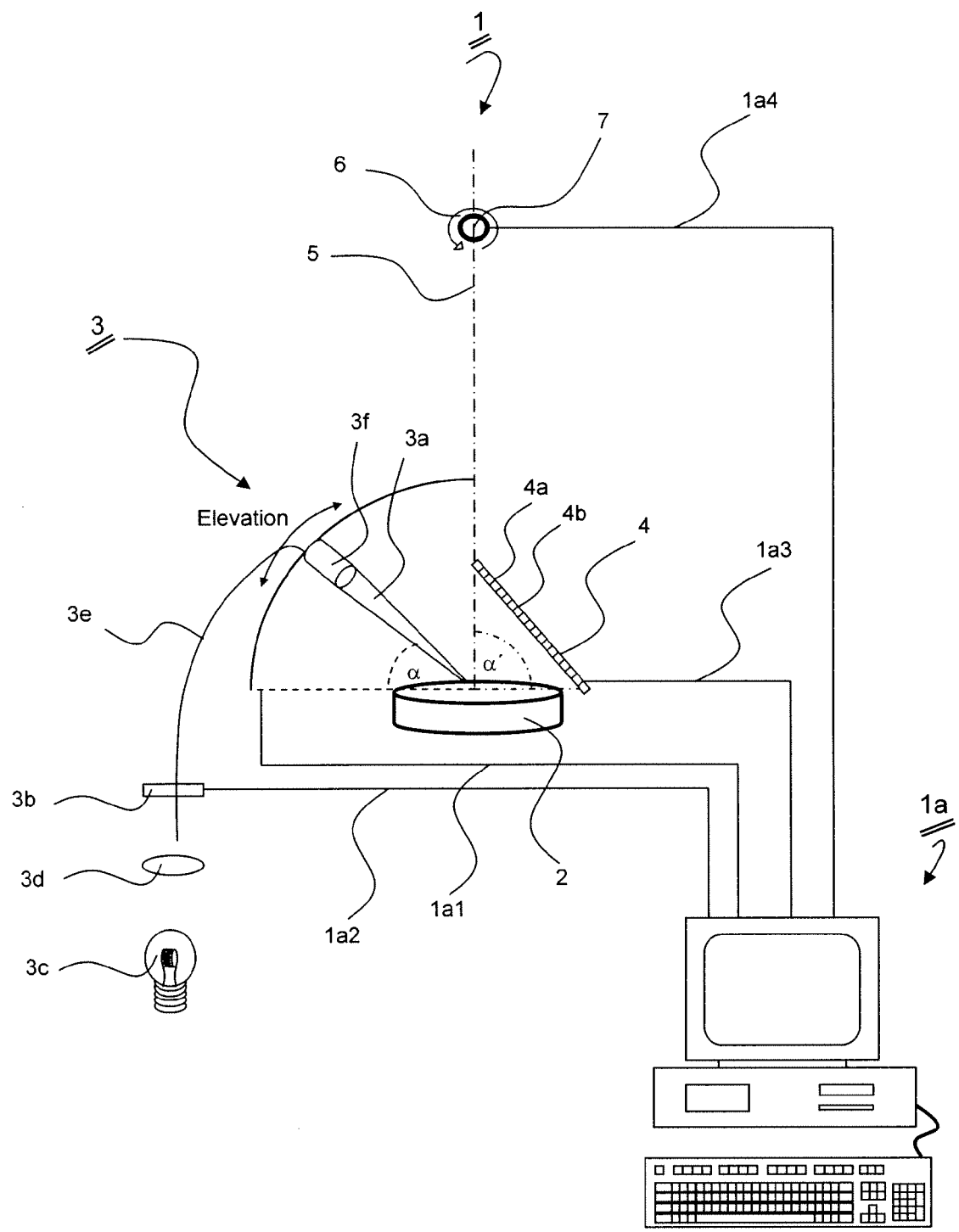

This application is related to and claims the benefit under 35 U.S.C. §119 and 35 U.S.C. §365 of International Application No. PCT/DE2006/002017, filed Nov. 17, 2006.

DESCRIPTION

The invention at hand concerns a claim as described in the preamble and involves a bidirectional reflectance distribution meter as well as measurements of reflectance distribution.

A glossy object seems to vary in brightness depending on the position in which the observer sees a light source hit the glossy object. This is a fact that can be observed everywhere, in the context of high-gloss magazines, metal surfaces, etc. It is possible to describe and characterize this gloss behavior by specifying reflectance distribution. Regarding all pairs of spatial direction, it indicates how light, which illuminates an object from a specific spatial direction, is being radiated to another spatial direction by means of the illuminated object. For example, an ideal mirror follows the known relationship of angle of incidence equals angle of reflection, whereas in one direction transverse to light beam deflection no light is being collected. This is different with matt or dull surfaces which reflect merely a small amount of the light, as in a mirror, while at the same time the surface largely diffuses the light. As a result, light can reach also other areas, not only those that are in the specific direction of light beam deflection, whereas with ideal reflectance such light beam deflection would occur. This gloss behavior offers us extensive information about an observed object. In order to generate realistic computer-generated images it is very important to precisely observe the gloss behavior. This is especially the case if the observer has the opportunity to watch a computer-generated image for an extended period of time, as is the case, for example, with freeze-images or advertising photos. In this context, it is possible to achieve realistic results only if information is available for the particular gloss behavior of a specific surface, such as a new design of an automobile the appearance of which should be computer-generated for different finishes.

Bidirectional reflectance distribution meters have the capacity to determine the gloss behavior of a sample.

Known bidirectional reflectance distribution meters irradiate samples in such a way that the light source gradually describes a curvature over the sample. Consequently, the light source illuminates the sample using pre-determinable elevation. This has the objective of determining the sample's light reception for each point of the hemisphere arranged above the sample. For this purpose, a light receiver can be moved around the sample, rotating it relative to the light source like the hands of a clock on the face of which one could imagine the sample to be. At the same time, its elevation under arch-like movement over the sample must be gradually adjusted. Known systems, which determine bidirectional reflectance distribution in this way, are precise but expensive, complex, large and slow.

It would be desirable to specify a bidirectional reflectance distribution meter by means of which precise measurements of the gloss behavior of a sample could be achieved quickly and at a reasonable price.

The invention at hand has the objective to provide a new process for industrial application.

The solution to the problem is claimed in an independent form. Preferred embodiments are included in the sub-claims.

A first basic idea of the invention at hand suggests a bidirectional reflectance distribution meter having a light source, which illuminates a sample using pre-determinable elevation and a light receiver, which can be moved relative to the light source in order to receive light from the sample. The light receiver of said bidirectional reflectance distribution meter comprises a plurality of receiver elements to receive simultaneously a broad elevation angle range and at least one light receiver element can be moved by the light receiver relative to the light source around an axis that extends generally vertical to the sample.

Consequently, a first basic idea can be seen in finding that a precise reproduction of the illuminated spot is not required to determine the gloss characteristics of a body. Instead, it has been established that it is possible, even without precise reproduction of this light spot on a receiver, to perform measurements which are completely adequate even for freeze-images and extended views without using such imaging optics. This allows the light receiver to be equipped with several receiver elements arranged closely together. Consequently, it allows for simultaneous reception of a broad elevation angle range, which can be measured angle-resolved by the majority of receiver elements. By preferably relinquishing larger optical displays and the like, the receiver elements can be arranged close to the sample which allows for an angle-resolved reception of a very broad elevation angle range. As a result, only one rotation is required between light receiver and light source around an axis running usually vertically to the sample. Consequently, instead of the previously required reading of a two-dimensional field, it is only necessary to perform a single rotation or deviation and thus a measurement with a single mobility degree. This, in turn, results in the fact that the entire structural assembly can be considerably simplified because it no longer requires such complicated mobility mechanism and/or sensor system which allows for further diminishment, simplification and price reduction of the device as a whole.

Preferably, the light source emits a light spot which can be focused on the sample. If the light irradiated on the sample by an illuminant is directed through filament, the general assembly is further simplified because it is not required to move the entire illuminant together with the mounting, etc.

It is possible to provide spectral filter media in the optical path between the illuminant of the light source and the sample. By means of said spectral filter media, light from predetermined spectral intensity distribution can be selectively irradiated on the sample. If filter wheels or the like are used as spectral filter means, it is possible to measure in short succession the bidirectional reflectance distribution with different wavelengths.

If the sample is illuminated with a light beam which is focused on the sample with approximately vertical incidence, the illuminated spot is magnified with very little illumination elevation, i.e., almost grazing illumination, without using additional measures. Preferably, therefore, means are provided for reducing the light source-induced errors which occur with little light source elevation. In a first model, the image errors with oblique incidence, i.e., so-called astigmatism, can be compensated, for which, for example, a cylindrical lense or the like can be arranged in the optical path before the sample. Alternatively and/or additionally, it is possible to perform a numerical correction on the ultimate large light spot, i.e., numerically correcting the actually collected raw data. This can be performed according to the type of a convolution, whereas raw data for other main angles of incidence can also be analyzed. If required, geometry and dimensioning of the measuring signal and the sample have to be taken into consideration. It is also possible to design a very small sample and arrange it on a stick or needle shaped carrier on a dark subsurface.

Typically, the light receiver is designed as a field with several receiver elements. To this end, in a preferred model, light receiver fields can be used, as they are already available per se. In particular, it is possible to use CMOS or CCD light receiver fields.

A particularly preferred model uses linear light receiver fields. On the one hand, this is preferred because it minimizes shading of the sample with determining backscatter, that is, with light receivers arranged close to the light source. On the other hand, it is preferred because it even allows minimizing backscatter, etc. from the light receiver to the sample, which would otherwise be a disturbing factor with the close distances typically provided between light receiver and light and light transmitter during the reception of the desired broad elevation angle range.

Typically, the light receiver collects an elevation angle range of at least 15°. This is sufficient to obtain useful information for specific applications. However, it possibly requires a movement of the light receiver field if an approximate bidirectional reflectance distribution is to be measured in its entirety. Therefore, preferably elevation angle ranges of at least 30°, in particular 45°, are being collected. In preferred cases, even angles of approximately 90° can be collected. To this end, a lowermost light receiver field can be arranged approximately on the level of the sample and the light receiver extends close to, or beyond the ordinary scope of the illumination light spot. With equally spaced light receiver elements in the light receiver field, errors can occur in insofar as not every light receiver observes exactly the same angle range. However, the resulting inaccuracies, if they are not compensated, are still acceptable for supersensitive measurements, for instance, of car paint or other extremely glossy paints.

For specific, sufficiently thin and translucent samples and adequate sample types, which do not affect the shadow course, it would be expedient to use an elevation angle range of more than 90°, whereas part of the observation occurs below the sample. This can be achieved by using a light receiver field which refracts up to under the sample level or, preferably, by using two light receiver fields which impinge at least approximately at the sample level, each of which is bending toward the sample axis, resulting from a lateral view in "<" form. With such arrangement, it is possible to measure simultaneously also transmittance for bidirectional reflectance. This is especially advantageous with translucent samples, such as plastic materials, which are so thin that scattering in the sample does not cause any highly significant optical effects. Alternatively and/or additionally, the light source can be moved in such a way that it illuminates the sample from below from an adequate, negative elevation angle in order to collect at the time the transmittance and the arrangement. With regard to the desired mechanical and electrical complexity, as well as the required measuring speed, a selection can be made between light source movement toward negative elevation angles or larger light source fields collecting negative elevations. Independent of the potential collection of transmittance, the illumination elevation angle can also be changed by changing the sample inclination. In this case, the sample can, for example, be situated on a table which rotates around an axis located in the sample level.

In a preferred model, the light receiver is inclined against the ordinary scope toward the sample. The light receiver will especially cover an area of at least approximately 90° elevation observation angle range, if required on one side of the sample. If an area of less than 90° elevation observation angle range is covered, the sample can also be illuminated from above at right angle, if required. However, if an area of at least 90° is covered, the sample is shadowed if it is illuminated from above at right angle. However, the shadowed areas do not necessarily have to be measured in order to specify realistic computer-generated freeze images having highly precise gloss behavior. Rather, interpolation for the shadowed areas is usually uncritical.

The light receivers—which, preferably are designed with a small edge and which are therefore usually needle shaped—do not have to cut exactly the axis running vertically on the sample at the light spot. However, preferably, the receiver needle gets at least very close to this imaginary axis, which would correspond to a warped position with the typically preferred inclination of the receiver element toward the sample axis.

It is also possible to arrange the linear receiver fields in an arch in order to diminish the possibility of an angle deficiency.

In a preferred model, the entire elevation range can be observed with one and the same sensitivity or amplification and/or time integration. In this way, no errors occur by changing an amplification range, etc. The linear receiver fields with high dissolution and adequate dynamic are already in use in commercial products of the applicant.

Preferably, the light source consists of a rotatable, especially controlled, pivot-arch center for the purpose of changing the elevation around the sample. Alternatively and/or additionally, the sample can be rotated or swiveled, for example, with only gross light source elevation changes having minor arch amplitudes and, for example, oscillating particularly around an axis located on the sample level or at least parallel and close to the axis of the sample. Furthermore, the light source and the light receiver are arranged in such a way that they are rotatable, swivel-mounted or pivot-mounted. As a result, an imaginary angle having the illuminated spot of the sample as peak changes at least between approximately 0° and 180°. That the change only amounts to between approximately 0° and 180° is based on the fact that the light receiver elements, which preferably are arranged at the sample in shorter distance than the front elevation of the light source, are exposed to minor shadowing. The rotation axis of the relative movement of light transmitter and light receiver does not have to be exactly vertical to the sample; however, it simplifies expansion and design. Clearly preferred are deviations under 10°, especially under 5°, and particularly smaller 0.5°.

Preferably the light receiver elements receive light without imaging optics.

Subsequently, the invention is described in exemplary fashion only by means of the drawings. It is shown FIG. 1: a bidirectional reflectance distribution meter of the invention at hand FIG. 2: an image of reflectance distribution for a fixed illumination elevation (here: α=40°) and with interpolated values in shadowed areas.

According to FIG. 1, a bidirectional reflectance distribution meter 1, comprises a light source 3 illuminating a sample 2 using predetermined illumination elevation α and a light receiver 4 which is movable in relation to the light source for the purpose of light reception from the sample 2. For simultaneous reception of a broad observation elevation angle range α', the light receiver comprises a plurality of receiver elements (for reasons of clarity indicated only at 4a, 4b) and at least one of light source 3 and light receiver 4 is movable around an axis 5 (generally vertical toward the sample 2) as indicated by arrow 6.

In its preferred, displayed model, the bidirectional reflectance distribution meter 1 is portable. It is therefore small enough to be placed on a customary worktable. Consequently, in the preferred and displayed embodiment, the distances between light source 3 and sample 2 do not exceed approximately 50 cm from the point of emission of the light beam 3*a* to the sample 2. As indicated through 1*a*, the bidirectional reflectance distribution meter is computer-controlled or operated. The elevation $\alpha$ of the light source can be changed by means of a computer-controlled electromotor, as indicated through line 1*a*1. The spectral intensity distribution of the light beamed to the sample 2 by means of the light source 3 can also be changed, indicated through line 1*a*2 which is directed as a control line to a filter wheel 3*b* powered by an electric motor. Provision has been made for a line 1*a*3 that feeds in appropriate signal-conditioned form the signals (which represent irradiance intensity) of the majority of receiver elements 4*a*, 4*b* to the central data processing stage. The relative movement between light receiver 4 and light source 3, indicated through arrow 6, can be predetermined by means of a control line 1*a*4, which supplies an electric motor 7 with control and performance signals. In addition, sensors have been provided to collect measurement relevant parameters, such as light source elevation, as well as sensors to utilize intensity in order to standardize light source intensity, etc. The signals of these sensors can also be analyzed.

Apart from dedicated interfaces, the control and data evaluation unit 1*a* has to be designed as a customary online-computer, PC or laptop. In this respect it is suitable to perform required numerical corrections of measurement values. Consequently, the control and data evaluation unit 1*a* comprises or forms a corrective stage to perform numerical corrections of raw data collected.

In the embodiment at hand, the sample 2 is a sample of car paint applied to a suitable carrier. The gloss and albedo behavior of the car paint has to be analyzed so that subsequently the measuring data can be used for computer generation of images of vehicles to be painted with this paint. In a preferred embodiment and the distances mentioned above, the sample can have a size of approximately 5×5 cm or even smaller. A very small sample preferably arranged on an absorbing carrier, which converges at the bottom or which is stick-shaped, can alleviate the astigmatism problem of the illumination astigmatism.

The sample 2 has to be arranged in such a way that its center coincides with the axis 5 around which the light receiver 4 or light source 3 are rotating or pivoting. In the embodiment described, the sample is motionless and lies usually horizontal, i.e., a light beam from the light source 3*a* runs under an elevation angle of $\alpha=0$ parallel to the sample 2, while at an elevation angle of $\alpha=90°$, the surface of the sample 2 receives vertical illumination.

If samples other than paint samples have to be analyzed, appropriate retainers can be provided for the samples, for example, for the purpose of keeping textile material in straight and tight position in order to analyze its bidirectional reflectance behavior.

First of all, the light source 3 comprises an illuminant 3*c* which FIG. 1 shows to be a light bulb. Reasonably, bright illuminants having high light density and adequate spectral distribution are preferred in practical realization. The light from the illuminant 3*c* is generated, if necessary after collimation as indicated through the lens 3*d*, spectrally filtered or it is generated with adequate spectral distribution as indicated through the filter 3*b*, which is here realized as a filter glass arranged on a filter wheel 3*b* which, in turn, is positioned above a control line 1*a*. It is also possible to use spectrometers or to achieve desired spectral distribution by activating and deactivating appropriate light sources, such as colored laser diodes, etc. In the embodiment shown, the light arranged, as required and desired, with selected spectral intensity distribution is directed via an optical fiber 3*e* onto an output coupler 3*f* which allows the light to focus on the sample 2. The object lens, i.e., the output coupler 3*f*, is attached to a rotary arm powered by an electric motor, in particular a multiphase motor in such a way that, by controlling the unit 1*a*, an arch can be measured above the sample and with the sample as center point, describing elevations approximately of between 0° (almost parallel incidence toward the sample) and 90° (almost vertical incidence). The illuminated light focuses on the sample in such a way that with approximately vertical incidence-of-light, i.e., an elevation of $\alpha=90°$, the smallest possible focal spot is obtained on the sample. Without additional measures, because of the grazing incidence with minor elevation, this results in focal spot amplification on the sample, i.e., astigmatism occurs.

The receiver 4 as linear field of light receiver elements is arranged close to the sample to be able to collect the light that the sample reflects back into the room. To this end, the light receiver elements have a distance to the sample that is considerably smaller than the focal width of the output optics 3*f* of the light source 3. In a practical model, 1,024 light-sensitive elements are arranged in the light-sensitive receiver field. With adequately compact arrangement of the light receiver 4 to the sample 2 of, for example, not more than 5 cm distance, this number allows for adequately high dissolution. By means of suitable light receiver fields with adequately high dynamic range (as they are already used as linear arrays in commercial products, such as cameras), a sample can be collected without changing an amplification factor or other adjustments in the areas receiving very small amounts of light from the sample, for example, with an observation elevation angle $\alpha'$ deviating significantly from the elevation angle of incidence $\alpha$, as well as with direct reflectance.

The light receiver 4 is pivotally arranged around the axis 5. In the embodiment depicted, as far as possible, the rotary range is restricted to 360° and lower, for example, 190°. At the same time, ranges above 180° allow for an overlap. With homogeneous samples, the sample can be rotated together with the light receiver. If the sample is not homogeneous, as is, for example, the case with textile materials having structuring weaving direction, the sample can be retained and the light receiver 4 can be rotated around an axis 5 relative to the sample and the light source 3. To this end, the light receiver 4 is arranged and adjusted in such a way that the highest of the light-sensitive elements are located on the axis 5 or at least near the axis 5, while the lowest of the light-sensitive elements of the light receiver 4 are designed for an observation elevation angle $\alpha'$ of approximately 0°.

As preferred, for rotation around the axis 5, it is possible to provide a multiphase motor 7 with a step size and step frequency controlled via a line 1*a*4. The step sequence is determined in such a way that the integration time required for the respective measuring purposes can be obtained in each position of the light receiver 4 relative to the light source 3. As preferred, the step size is here adjustable, taking into account various requirements to the measuring dissolution.

The arrangement is used as follows:

First, a sample 2 is arranged on the sample retainer. Next, with an elevation of approximately $\alpha=90°$, light is focused on the sample 2. The maximum elevation angle can only approximately amount to 90° and not exactly to 90° because the light receiver 4 shadows the incidence-of-light at exactly 90°. Subsequently, a first spectral intensity distribution is selected and the receiver 4 by rotating the motor is arranged in a diametrical position toward the light source 3. Then it is required to wait for an integration time. During this period, for each light receiver element the signal received at the light receiver 4 is integrated respectively. Consequently, this signal represents a measuring unit for the respective light which the sample radiates to a light receiver element, i.e., the light radiated to a specified observation elevation angle range $\alpha'$. The light receiver field 4 is read, the data stored and, under rotation, the multiphase motor 7 is moved a predetermined angular step around axis 5. As a result, the light receiver 4 has been rotating a little around the axis 5. Another measurement is taken and the values are read. This is repeated until the light receiver also observes approximately from the beaming direction. If the diametrically opposite position is depicted with $\beta=0°$, it is possible to measure to up to approximately $\beta=180°$. At range $\beta=180°$, the sample is shadowed by the light receiver 4. As far as possible, the shadowed area can be reduced even with customary linear light fields, if the light receiver is not arranged in a customary IC socket, which has considerable width. Instead, it is important that the carrier, which lacks electrical connections to the light receiver, etc., is as narrow as possible.

The light source 3$f$ is then powered down an angular elevation step $\alpha$ and moved in the range $\beta$ of between 0 and approximately 180° for the purpose of measuring the light receivers. Altogether, in this way, measurements can be collected for an irradiation elevation angle $\alpha$ of between approximately 90° and approximately 0°, an observation elevation angle $\alpha$ relative to the direction of arrival of $\beta=0°$ to 180°, each simultaneous for an observation elevation angle $\alpha'$ of between 90° and approximately 0°. With an illumination elevation angle $\alpha$ of approximately 0°, without refocusing, a considerably enlarged light spot of the light source is being obtained. This can be reduced by using adequate imaging optics, such as cylindrical lenses, which, with minor elevation, i.e., $\alpha$ approximately 0°, produce focal spot reduction and/or by means of numerical correction of the collected values after acceptance of the respective parameter fields. Such numerical operations, described as convolutions, make additional optical elements expendable.

Figure 2:
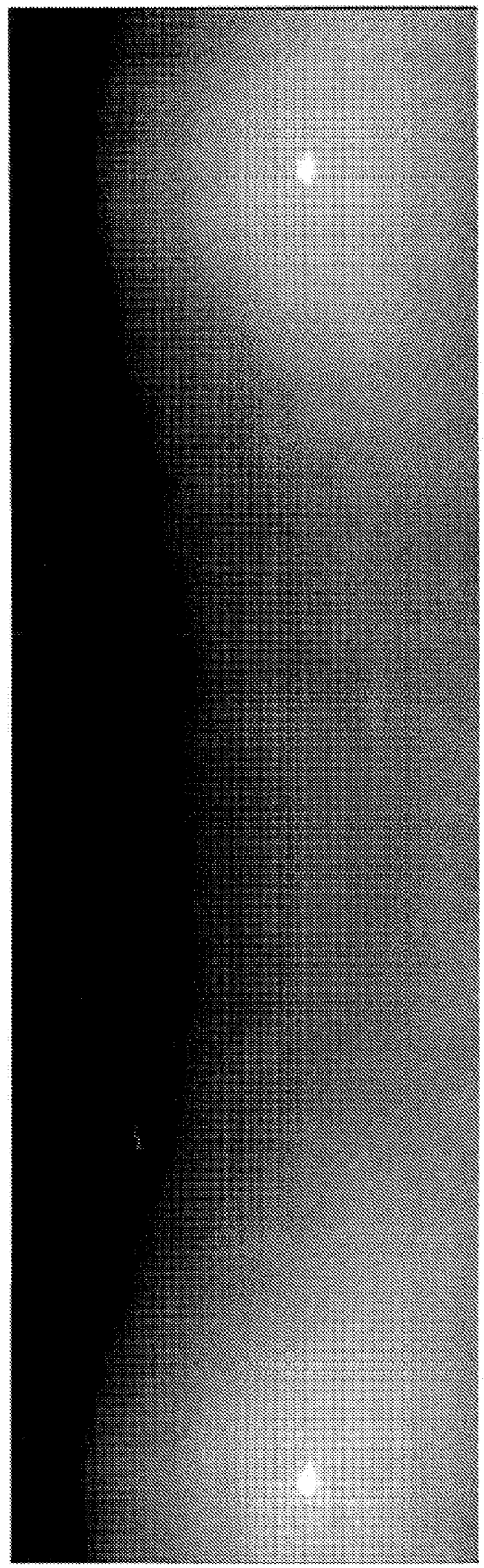

FIG. 2 shows an example of the data record obtained with an invention-based device. It shows the raw data determined with an elevation angle of incidence of $\alpha=40°$ at revolving the illuminated sample. At this point, no astigmatism correction, etc. have been performed. However, interpolation has been performed for the data in which the light receiver moving between light source and sample has been shadowing the sample. On the right and left side, the raw data image shows two lighter bright points. Those two bright spots are included in the raw data record because a rotation of more than 360° has been initiated in order to achieve an overlap. The fact that the actual bright spots are measured twice is especially advantageous because, on the one hand, it is especially easy to achieve an overlap and, on the other hand, it is required to average measurements for the especially important bright spots and their surrounding area.

With structured samples, reflectance can even depend on the microstructure of the sample. It is also possible to use the values obtained with the device described above to simulate appropriate values.

With translucent, i.e., not fully opaque samples, it is possible to perform measurements having elevation angles smaller than zero for incidence-of-light elevations and/or observation elevations, if the device is appropriately designed. This can occur through adequately large and sufficiently expanding light reception fields, in particular also through light transmitted through the sample simultaneously with reflected or dispersed light, as well as through respectively movable transmitters which irradiate with elevation angles under zero. Preferably, the negative elevation angles under which to irradiate and/or observe also comprise at least 90°, i.e., allowing for an expansion of light reception up to the sample axis. However, like the positive elevations. The range of observed negative elevations can turn out to be smaller, resulting in especially gradual or progressive measurements. If required, a light reception field can be used successively for measurements of transmittance and reflectance, for example, under rotation around an axis which lies on the sample level.

The invention claimed is:

1. A bidirectional reflectance distribution meter, comprising a light source for illuminating a sample under a predetermined elevation and a linear light receiver having a plurality of receiver elements for receiving light from the sample wherein the light of the light source can be focused onto the sample, the light receiver is inclined against an axis perpendicular to the sample surface so as to observe a broad elevation angle range and the light receiver is movable relative to the light source.

2. The bidirectional reflectance distribution meter according to claim 1, wherein for the purpose of simultaneously collecting light, the light receiver is designed to comprise an elevation angle range of between 30° and approximately 90°.

3. The bidirectional reflectance distribution meter according to claim 1, wherein for the purpose of simultaneously collecting light, the light receiver is designed to comprise an elevation angle range of between 45° and approximately 90°.

4. The bidirectional reflectance distribution meter according to claim 1, wherein the light source can be rotated toward the elevation change in an arc running around the sample.

5. The bidirectional reflectance distribution meter according to claim 1, wherein it is arranged to receive light penetrating a sample, in particular light observed and/or activated using negative elevation angles.

6. The bidirectional reflectance distribution meter according to claim 1, wherein the light source is attached to spectral filter means in order to illuminate the sample with selected spectral intensity distribution.

7. The bidirectional reflectance distribution meter according to claim 6, wherein means are provided for reducing the light source-induced errors which occur with little light source elevation.

8. The bidirectional reflectance distribution meter according to claim 6, wherein the light receiver is designed as a light receiver field.

9. The bidirectional reflectance distribution meter according to claim 1, wherein means are provided for reducing light source-induced errors which occur with little light source elevation.

10. The bidirectional reflectance distribution meter according to claim 9, wherein the means for reducing light source-induced errors which occur with little light source elevation comprises a cylindrical lens for astigmatism compensation in front of the sample.

11. The bidirectional reflectance distribution meter according to claim 10, wherein the means for reducing comprise a corrective stage to perform numerical corrections of raw data collected.

12. The bidirectional reflectance distribution meter according to claim 9, wherein said means comprises a corrective stage to perform numerical corrections of raw data collected.

13. The bidirectional reflectance distribution meter according to claim 9, wherein the light receiver is designed as a light receiver field.

14. The bidirectional reflectance distribution meter according to claim 1, wherein for the purpose of simultaneously collecting light, the light receiver is designed to comprise an elevation angle range of between 15° and approximately 90°.

15. The bidirectional reflectance distribution meter according to claim 1, wherein the light receiver cuts an axis which points vertically to the sample at the illumination light spot and/or is arranged in warped fashion with only minor distance from the sample.

16. The bidirectional reflectance distribution meter according to claim 1, wherein the light source can be rotated toward an elevation change.

17. The bidirectional reflectance distribution meter according to claim 1, wherein the light source and/or light receiver are arranged in pivoting, swiveling and/or rotating fashion.

18. The bidirectional reflectance distribution meter according to claim 1, wherein the light receiver elements collect light without imaging optics displaying the light spot of the sample.

19. The bidirectional reflectance distribution meter of claim 1, wherein it is arranged to receive light penetrating a sample.

* * * * *

UNITED STATES PATENT AND TRADEMARK OFFICE
CERTIFICATE OF CORRECTION

PATENT NO. : 7,884,943 B2  
APPLICATION NO. : 12/094443  
DATED : February 8, 2011  
INVENTOR(S) : Gerhard Bonnet Page 1 of 1

It is certified that error appears in the above-identified patent and that said Letters Patent is hereby corrected as shown below:

Claim 7, Column 8, line 49, delete "the"

Signed and Sealed this  
Nineteenth Day of April, 2011

David J. Kappos  
*Director of the United States Patent and Trademark Office*